(12) United States Patent
Koennecke

(10) Patent No.: US 7,702,225 B2
(45) Date of Patent: Apr. 20, 2010

(54) DEVICES TO FACILITATE ALIGNMENT AND FOCUSING OF A FUNDUS CAMERA

(75) Inventor: Greg Koennecke, Hobart (AU)

(73) Assignee: Vision Instruments Pty Ltd, Hobart, Tasmania (AU)

( * ) Notice: Subject to any disclaimer, the term of this patent is extended or adjusted under 35 U.S.C. 154(b) by 579 days.

(21) Appl. No.: 10/584,959

(22) PCT Filed: Dec. 31, 2004

(86) PCT No.: PCT/AU2004/001825

§ 371 (c)(1), (2), (4) Date: Apr. 30, 2007

(87) PCT Pub. No.: WO2005/065528

PCT Pub. Date: Jul. 21, 2005

(65) Prior Publication Data

US 2007/0253688 A1    Nov. 1, 2007

(30) Foreign Application Priority Data

Jan. 2, 2004    (AU) .............................. 2004900009

(51) Int. Cl.
*A61B 3/14*   (2006.01)
(52) U.S. Cl. ..................... 396/18; 348/78; 351/206; 351/208; 351/211
(58) Field of Classification Search ......... 351/206–208, 351/211, 214, 220–221; 396/18; 348/78
See application file for complete search history.

(56) References Cited

U.S. PATENT DOCUMENTS

| | | |
|---|---|---|
| 3,925,793 A | 12/1975 | Matsumura |
| 3,936,844 A | 2/1976 | Matsumura |
| 4,187,014 A | 2/1980 | Kato et al. |
| 4,198,144 A | 4/1980 | Matsumura et al. |
| 4,251,139 A | 2/1981 | Matsumura |
| 4,252,420 A | 2/1981 | Kohayakawa |
| 4,253,743 A | 3/1981 | Matsumura |
| 4,257,688 A | 3/1981 | Matsumura |
| 4,436,388 A | 3/1984 | Takahashi et al. |
| 4,452,517 A | 6/1984 | Kohayakawa |
| 4,469,416 A * | 9/1984 | Isono ......................... 351/206 |

(Continued)

FOREIGN PATENT DOCUMENTS

EP        0412667 A1    2/1991

(Continued)

*Primary Examiner*—W. B. Perkey
*Assistant Examiner*—Bret Adams
(74) *Attorney, Agent, or Firm*—Joseph J. Mayo; Dalina Patent Group

(57) ABSTRACT

A fundus camera is provided with a focus aid mark projection system (5, 9, 10, 11, 12, 13) that includes a focus aid mark focussing lens (10) and other optical components such that the focus aid mark focussing lens (10) is attached to the focussing lens (6) of the imaging system and moves with that lens, thereby maintaining the focal planes of the focus aid mark projection system and the imaging system co-planar. An associated alignment mark projection system (35, 34, 33, 32) includes optics that utilize part of the existing fundus camera illumination system (35) to project a plurality of alignment marks onto the iris of the subject eye.

6 Claims, 3 Drawing Sheets

U.S. PATENT DOCUMENTS

| | | |
|---|---|---|
| 4,544,248 A | 10/1985 | Nunokawa |
| 4,591,249 A * | 5/1986 | Takahashi et al. ............. 396/18 |
| 4,673,264 A | 6/1987 | Takahashi |
| 4,756,613 A | 7/1988 | Okashita |
| 5,742,374 A | 4/1998 | Nanjo et al. |
| 5,751,396 A | 5/1998 | Masuda et al. |
| 7,303,279 B2 | 12/2007 | Koennecke |
| 2002/0060778 A1 | 5/2002 | Su et al. |
| 2007/0183760 A1 * | 8/2007 | Mizuno et al. ................ 396/18 |
| 2008/0018854 A1 * | 1/2008 | Matsumoto ................. 351/206 |

FOREIGN PATENT DOCUMENTS

| | | |
|---|---|---|
| WO | WO 9524152 A1 | 9/1995 |
| WO | WO 0195791 A1 | 12/2001 |

* cited by examiner

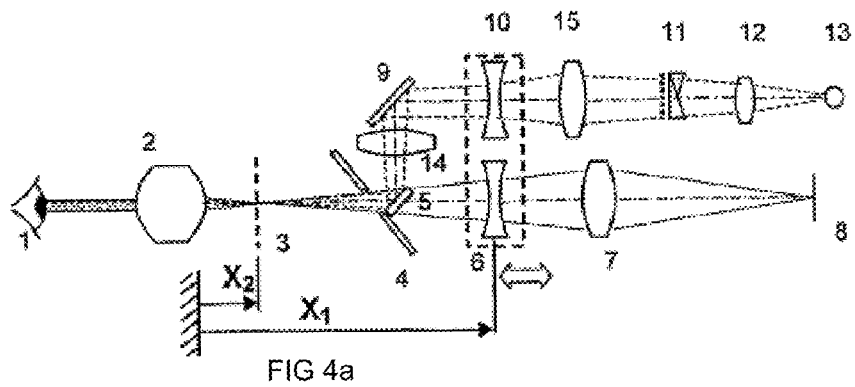
FIG 4a
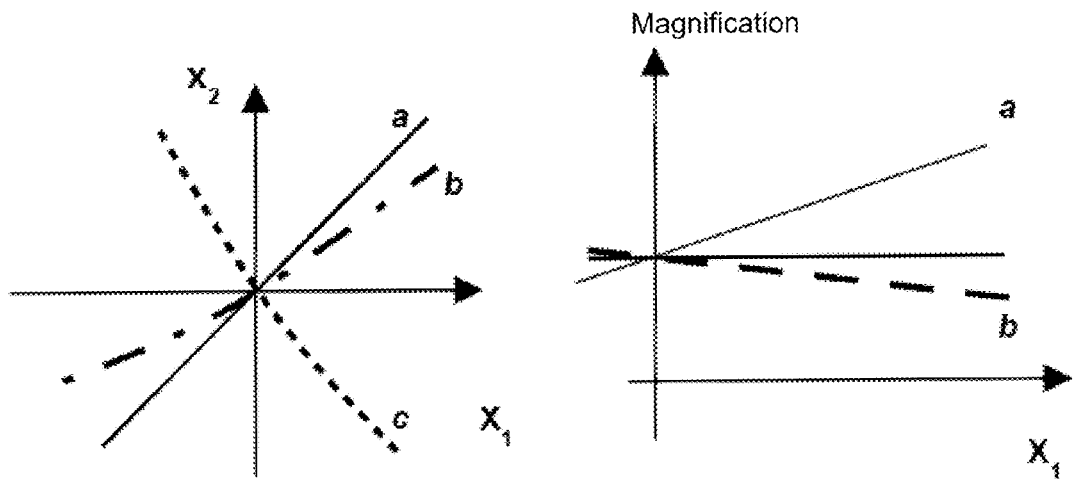
FIG 4b
FIG 4c
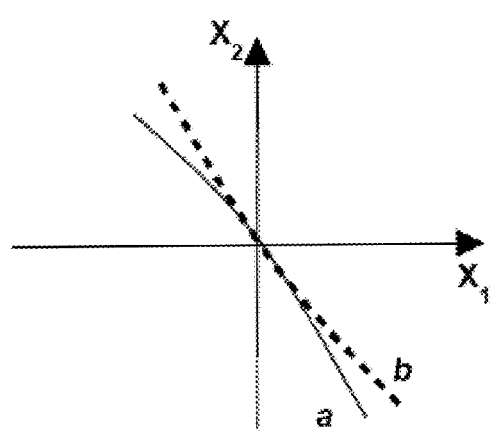
FIG 4d

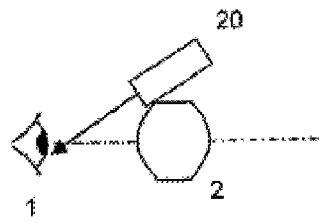
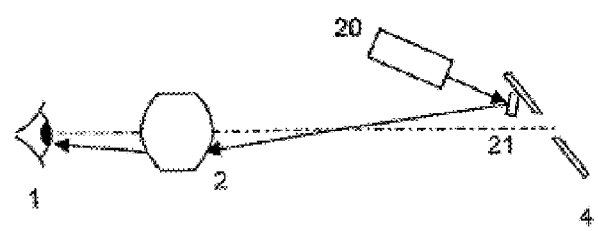
FIG 5a
PRIOR ART
FIG 5b
PRIOR ART
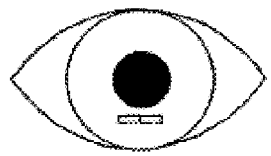
FIG 6a
FIG 6b
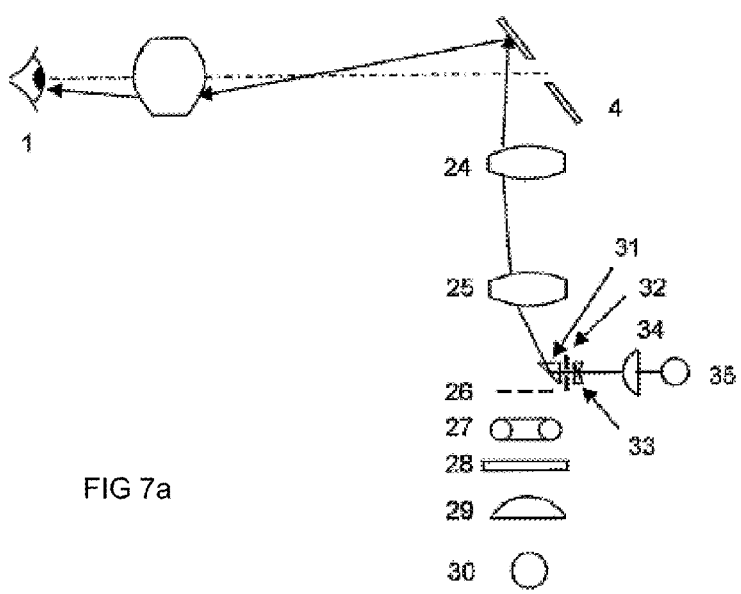
FIG 7a
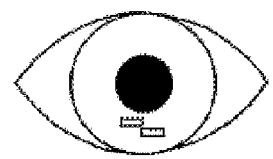
FIG 7b
FIG 8a
FIG 8b

DEVICES TO FACILITATE ALIGNMENT AND FOCUSING OF A FUNDUS CAMERA

TECHNICAL FIELD

This invention relates to improvements in devices for alignment and focussing of a fundus camera.

A fundus camera is used to capture an image of the fundus (posterior portion of the eye, including the retina and blood vessels). This fundus image can be examined by a third party or compared to fundus images taken at an earlier date, to facilitate diagnosis of retinal disease. The fundus camera comprises an objective lens to form an image of the fundus of the eye, other lenses to form an image on the recording plane of a camera, and an illumination system to project light into the eye so that the fundus image is sufficiently bright that an image may be captured on the camera. To enable a useful image to be formed without unacceptable reflections from the anterior parts of the eye (including the cornea, iris and vitreous lens) the fundus camera must be aligned very accurately. For capture of fundus images without mydriasis to dilate the pupil, the required accuracy of fundus camera alignment is difficult to achieve without features to guide the operator in the focus and alignment of the fundus camera. Various devices have been proposed to project marks onto the eye to facilitate alignment and focus. These devices have various disadvantages in complexity or performance.

BACKGROUND ART

To facilitate accurate focussing of the fundus camera, one or more marks may be projected onto the eye fundus and the image of these marks may then be observed though the fundus camera. Further, split prisms may be provided within the line projection system such that the image of the projected marks on the eye fundus appears as a split line if the camera is not correctly focussed, as discussed in U.S. Pat. No. 3,925,793. The optical components for such a system for projecting a mark to aid focussing may be separate from the illumination system and combined with an afocal lens system, such that the focus of the viewing system and the focal plane of the projected line system may be maintained coincident as the focus of the viewing system is adjusted as discussed in U.S. Pat. No. 4,187,014. The afocal lens system required for this system has a disadvantage that the magnification of the image appearing at the camera imaging plane changes through a large range as the focus is adjusted and this varies the area of the fundus and the apparent brightness of the image through a large range. Alternatively, the optical components for such a system for projecting a line to aid focussing may be separate from all or part of the focussing and illumination systems and these optical components may be moved by cams or linkages or similar means such that the focus of the viewing system and the focal plane of the projected line system may be maintained coincident as the focus of the viewing system is adjusted as discussed in U.S. Pat. No. 4,436,388. This alternative allows the use of a lens of reduced or negative power as the focussing lens with a result that the change in image magnification is reduced, but the required cams or linkages increase the mechanical complexity of the system.

DISCLOSURE OF THE INVENTION

It is an object of this invention to provide a means of adjusting the focus of a projected mark focus aid system that is simple in construction while not requiring an afocal lens system to be used for the image focus adjustment.

According to the present invention, a first focus aid mark focussing lens separate to the image focusing system is connected to the image focus adjustment lens with a simple rigid arm or similar connection. Second and third fixed lenses may be placed either side of the focus aid mark focussing lens such that these lenses do not move with movement of the focus aid mark focussing lens. A focus aid mark is formed by a slit with a pair of deflecting prisms that deflect the light from the slit along separated optical paths such that two images of the slit are formed that are only aligned to form a single line image of the slit at a focal plane of the focus aid mark projection system. This focus aid mark is projected though the focus aid mark projecting lens system and through a system of mirrors and the fundus camera objective lens to form an image of this focus aid mark on the eye fundus. If the power of the focus aid mark focussing and second and third fixed lenses and the focus aid mark focussing lens are chosen correctly, the focus of the imaging system and the focal plane of the projected line system may be maintained coincident for any position of the image focus adjustment lens as the focus of the viewing system is adjusted by moving the image focus adjustment lens. The effect of the second and third fixed lenses is that the image focus adjustment system does not have to be an afocal system as specified in U.S. Pat. No. 4,187,014. Thus a design with a negative focus adjustment lens may be used with consequent reduced change in image magnification and image brightness when compared with the afocal imaging focus adjustment system. Also the geometry of the lens system and resultant focal plane can be controlled by correct choice of the lenses to allow sufficient length in the optical path for incorporation of the mirrors required to combine the imaging and projected focus mark aid optical paths in a practical instrument.

To facilitate accurate alignment of the fundus camera, one or more alignment aid marks may be projected onto the iris of the eye. Two alignment marks may be projected so that when the fundus camera is correctly positioned, the two alignment marks are coincident and in focus on the iris of the eye (U.S. Pat. Nos. 4,257,688; 4,252,420; 4,253,743). In a previous invention (U.S. patent application Ser. No. 10/710,003) such alignment marks have been implemented by mark projection optics that are either external or internal to the fundus camera optics. It is preferable that the alignment marks are projected from a source internal to the fundus camera and then through the objective lens to the subject eye to minimise the bulk of the instrument in the vicinity of the subject eye and minimise the number of additional optical components required to form the projected alignment marks. The projected alignment and focus marks may be formed in infrared light and the observation system includes a camera sensitive to infrared light, so that projection of the marks into the subject's eye does not cause the subject's pupil to contract.

It is an object of this invention to provide a means of implementing a projected alignment mark system that is simple in construction and compact by combining the alignment mark system with the illumination system that already exists in the fundus camera and generating the two alignment marks discussed in U.S. patent application Ser. No. 10/710,003 from one light source.

According to the present invention, the alignment targets are formed from an image of a slit, with a pair of deflecting prisms arranged adjacent to the slit as for the focus aid projection system discussed above to divide the light from the light source into two separate paths. Alternatively, the light from the light source may be divided into two separate paths by reflection from a pair of mirror surfaces adjacent to the slit, where the mirrors are rotated relative to each other about an axis passing through each mirror surface and orthogonal to the axis of the optical path. Light from the slit is combined with the light from the fundus illumination system by a mirror or prism such that the slit is conjugate with a first stop in the illumination system. Light from the slit then passes through the normal illumination system optics and is imaged onto the iris of the subject eye. When the fundus camera is correctly aligned an image of the first stop is formed in the plane of the eye pupil. An image of the alignment target slit is also formed on the iris of the eye. If the fundus camera is not correctly aligned, the image of the alignment target slit will be split into two lines because of the split prism adjacent to the alignment target slit.

To assist with understanding the invention, reference will now be made to the accompanying drawings which show at least one example of the invention.

In the drawings:

FIG. 1 shows one example of a fundus camera with projected focus aid marks as proposed in U.S. Pat. No. 4,187,014. Note that prisms 11 are shown rotated 90 deg about the optical axis, for clarity.

FIG. 2 shows an improvement of the design depicted in FIG. 1 where two additional lenses 14 and 15 are interposed either side of lens 10, as proposed in this patent FIG. 3a shows a variant of the improved design depicted in FIG. 2, whereby the moveable focussing lenses 6 and 10 are negative (diverging) lenses.

FIG. 4a is a reproduction of FIG. 3 with dimensions x1 and x2 defined.

Figure 2:
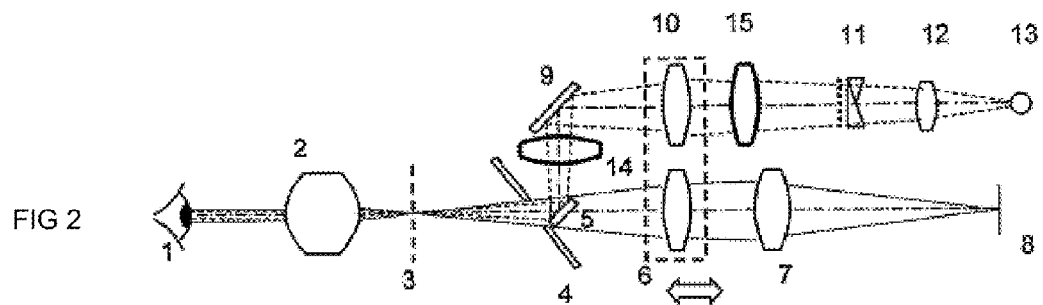
Figure 3A:
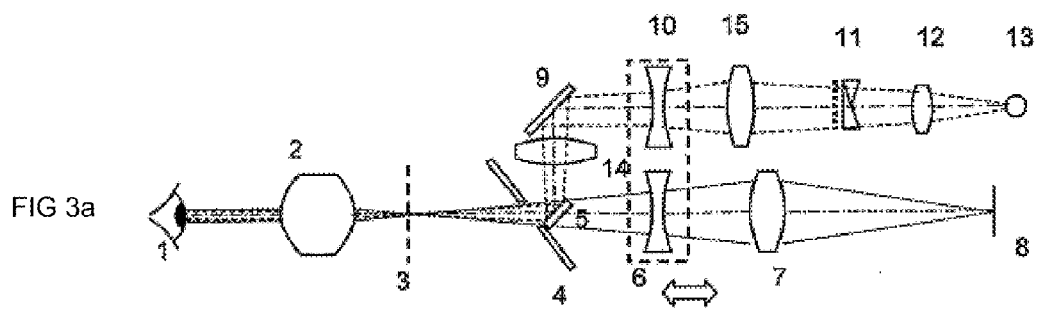
FIG. 3b shows how the focussing lenses 6 & 10 move together to focus the instrument on a new first image plane 3' for a non-emmetropic subject eye.
Figure 3B:
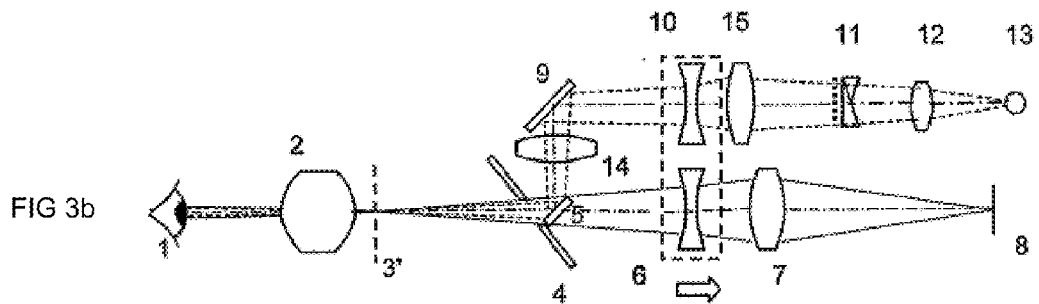

FIG. 4b is a graph of how the focussing lens position x1 varies with a movement of the first image plane x2. Line a indicates the relationship for the afocal system depicted in FIG. 1. Line b indicates the relationship for a non-afocal system as depicted in FIG. 2. Line c depicts the relationship for a system as depicted in FIG. 3, where lens 6 and 10 are of negative power.

FIG. 4c depicts the change in magnification of the image at the second image plane 8. Line a shows the change in magnification of the image for the afocal system depicted in FIG. 1, while line b depicts the reduced change in magnification for the preferred system depicted in FIG. 3.

FIG. 4d is a graph showing the effect of varying the ratio of powers of the fixed lenses 14 & 15 on the movement of focal plane of the projected focus aid mark with movement of the focussing lens 10. Line b indicates the relationship for a system with increased ratio of power of lens 15 over the power of lens 14, compared with that for line a.

FIGS. 5a & 5b depict the alignment target projection system as proposed in U.S. patent application Ser. No. 10/710,003. FIG. 6 shows the movement of the projected alignment marks on the eye cornea for the optical configurations shown in FIG. 5, as the fundus camera is moved closer to the eye.

FIG. 7 shows an improved alignment target projection system whereby the alignment marks are projected by an optical system that uses part of the illumination system of the retinal camera.

FIG. 8 shows the movement of the projected alignment marks on the eye cornea for the optical configurations shown in FIG. 8, as the fundus camera is moved closer to the eye.

MODE FOR CARRYING OUT THE INVENTION

Figure 1:
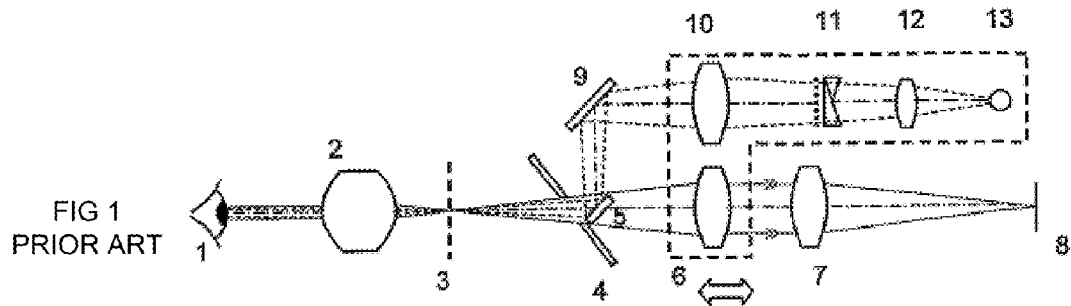

Referring now to the drawings, FIG. 1 shows one example of a fundus camera with projected focus aid marks as described in U.S. Pat. No. 4,187,014. FIG. 1 shows the imaging system of the fundus camera which comprises an objective lens 2 to collect light from the subject eye 1, a hole in the middle of an illumination reflecting mirror 4 to allow light to pass to the focussing lens 6 and imaging lens 7 and then to the imaging device 8. In this invention, the focus aid mark projection system is implemented via components 5,9,10,11,12, 13. Note that prisms 11 are shown rotated 90 deg about the optical axis, for clarity. Light from source 13 is condensed by the condenser lens 12 then split by the pair of splitting prisms and associated slit mask 11 into two diverging beams, then focussed by lens 10 and reflected by mirrors 9 and 5 so as to pass through two holes in mirror 4 either side of a central hole provided for the light passing to the imaging system 8 and thus to focus an image of the slit 11 at focal plane 3. The position of the focal plane 3 and thus the focus of the imaging system as defined by the image capture device 8 is set by moving the imaging focus lens 6. To maintain the focus of the projected focus aid mark as coplanar with the focus of the imaging system, components 10, 11, 12, 13 in FIG. 1 move in parallel with the imaging focussing lens 6. This system is only feasible if the focussing lens forms part of an afocal optical system, so that the to points on the imaging device 8 pass between elements 6 & 7 as parallel light bundles. This system has the claimed advantages of simplifying the mechanical design of the focus aid mark projection system, and separating the focus aid mark projection system from the illumination system of the fundus camera.

FIG. 2 shows and improvement which is a subject of this patent application, whereby two fixed lenses 14 & 15 are interposed either side of the moving focus aid mark focus aid mark focussing lens 10. This design allows freedom in the design of the image focussing system as this system does not have to be an afocal system as specified in the design depicted in FIG. 1. Also, only the lenses 10 and 6 are connected to move parallel in FIG. 2, so that the remainder of the focus aid mark projection system (items 11, 12 and 13) are fixed thereby simplifying the design of the fundus camera further. As depicted in FIG. 3, the improved design of FIG. 2 allows the use of a negative focussing lens 6, as is commonly used in fundus cameras. Said negative lens has the desirable effect of reducing the change in magnification of the fundus image at the imaging plane 8, thereby reducing the change in field of view and apparent brightness of the image. By varying the power of the two fixed lenses 14 & 15, the relationship between the movement of the focal plane of the focus aid mark and the movement of the focussing lens 10 can be varied. By correct choice of the fixed lenses 14 & 15, and the focussing lens 10, the focal plane of the focus aid mark and the focal plane of the imaging system can be maintained substantially coplanar as the focussing lenses 6 & 10 are moved together to adjust the focus of the fundus camera for different subject eye refractive error.

FIG. 4 depicts the relationships between movement of the focussing lenses 6 & 10 and consequent movement of the image focal plane 3. FIG. 4b is a graph of how the focussing lens position x1 varies with a movement of the first image plane x2. Line a indicates the relationship for the afocal system depicted in FIG. 1. Line b indicates the relationship for a non-afocal system as depicted in FIG. 2. Line c depicts the relationship for a system as depicted in FIG. 3, where lens 6 and 10 are of negative power. The slope of line c can be adjusted by changing the relative power of lenses 10, 14 & 15. FIG. 4c depicts the change in magnification of the image at the second image plane 8. Line a shows the change in magnification of the image for the afocal system depicted in FIG. 1, while line b depicts the reduced change in magnification for the preferred system depicted in FIG. 3. FIG. 4d is a graph showing the effect of varying the ratio of powers of the fixed lenses 14 & 15 on the movement of focal plane of the projected focus aid mark with movement of the focussing lens 10. Line b indicates the relationship for a system with increased ratio of power of lens 15 over the power of lens 14, compared with that for line a. This shows that the movement of the focal plane of the projected focus aid mark can be adjusted to match the movement of the focal plane of the fundus camera imaging system by correct choice of power of lenses 10, 14 & 15.

FIG. 5 shows alignment mark projection system as suggested in U.S. patent application Ser. No. 10/710,003. In FIG. 5a the alignment mark is projected directly onto the anterior surfaces of the eye by the alignment mark projection system 20. In FIG. 5b and alternative design is shown whereby the alignment mark projection system projects alignment marks from inside the fundus camera via a small mirror, through the objective of the fundus camera onto the anterior subject eye. If two alignment mark projection systems are provided, they can be arranged so that the two marks depicted in FIG. 6a form a single unbroken line on the iris of the subject eye 1, when the distance between the objective 2 and the subject eye 1 is correct, as depicted in FIG. 6b.

FIG. 7 shows an improved alignment mark projection system that forms two alignment marks from a single source 35 by passing light from the source through a condenser lens 34, a pair of prisms 33 and associated slit 32, through a reflecting means 31, and then through the fundus camera illumination system components represented by lens 25 & 24, and mirror 4. For completeness, the remainder of the normal fundus camera illumination system is depicted in FIG. 7 as a light source 30, condenser lens 29, IR pass filter 28, xenon flash lamp 27 and ring slit stop 26. The ring slit stop 26 would be configured as two partial segments as depicted in FIG. 7b, so as to stop light from lamp 30 from impinging onto that part of mirror 4 that has holes to pass light from the focus aid mark projection system as discussed above.

FIG. 8 depicts the appearance of the image of the projected alignment marks on the iris of the subject eye, where in FIG. 8a the line is in split into two displaced halves when the distance between the objective 2 and the subject eye 1 is not correct, and in FIG. 8b the projected alignment marks form a single unbroken line on the iris of the subject eye 1, when the distance between the objective 2 and the subject eye 1 is correct

The invention claimed is:

1. A fundus camera with a focus aid mark projecting system including:
    an objective lens for forming a subject eye fundus image at a plane within a fundus camera,
    an image focus adjustment lens configured to move to adjust the focus of the imaging system so that the imaging system is focused on the same plane as a first image of the subject eye fundus formed within the fundus camera,
    a moving focus aid mark focusing lens configured to move to adjust the focus of a focus aid mark so that it is coplanar with a focal plane of the imaging system, wherein the focus aid mark focusing lens is coupled to the imaging focus adjustment lens so as to move with that lens, and
    a focus aid mark projecting system comprising a light source and a condenser lens, wherein said light source and condenser lens are not coupled to the imaging focus adjustment lens.

2. The fundus camera of claim 1, further comprising one or more non-moving lenses in the same optical path as the focus aid mark focusing lens, wherein at least one of said one or more non-moving lens is positioned between said focus aid mark focusing lens and said condenser lens.

3. The fundus camera of claim 1 wherein said image focus adjustment lens and said focus aid mark focusing lens are negative lenses.

4. The fundus camera of claim 1 wherein the focus aid mark is formed as an image of a shaped aperture in the focus aid mark projection system.

5. The fundus camera of claim 1, further comprising a pair of deflecting prisms configured to deflect the light from a shaped aperture along separated optical paths such that two images of the shaped aperture are formed that are only aligned to form a single image of the shaped aperture at a focal plane of the focus aid mark projection system.

6. The fundus camera of claim 2 wherein powers of the focus aid mark focusing lens and one or more non-moving lenses in the same optical path are chosen such that the image of a shaped aperture forming said focus aid mark and a plane conjugate with a system imaging plane of said focus aid mark projection system are always substantially coplanar.

* * * * *